United States Patent

Korhummel et al.

[11] Patent Number: 5,962,739
[45] Date of Patent: Oct. 5, 1999

[54] PROCESS FOR THE PREPARATION OF N,N-DIALKYLAMINOPHENYL ALKANOLS

[75] Inventors: Claus Korhummel; Hanspeter Baier, both of Grenzach-Wyhlen, Germany

[73] Assignee: Ciba Specialty Chemicals Corporation, Tarrytown, N.Y.

[21] Appl. No.: 09/081,431

[22] Filed: May 19, 1998

[30] Foreign Application Priority Data

May 28, 1997 [GB] United Kingdom .................. 9710864
Nov. 4, 1997 [GB] United Kingdom .................. 9723170

[51] Int. Cl.$^6$ ................................................ C07C 209/00
[52] U.S. Cl. ............................................ 564/409; 564/443
[58] Field of Search ................................ 564/443, 409; 568/443, 409

[56] References Cited

U.S. PATENT DOCUMENTS 4,284,551 8/1981 Argentar .............................. 260/42.43
4,316,988 2/1982 Clinton ................................... 544/433

OTHER PUBLICATIONS

Kirk Othmer "Encyclopedia of Chemical Technology" vol. 22 pp. 233–238, 1983.
March Advanced organic Chemistry (textbook) p. 333, 1968.
Journal of Chromatography 319 pp. 382–386, 1985.
J Chem Soc Chem Commun "N Alkylation of Aniline Derivatives by use of Potassium Cation exchanged Y Type Zeolite" by Onaka, pp. 1202–1203, 1985.
Journal of the American Chemical Society, 97:11, May 28, 1975, pp. 3102–3108.
M.G. Seeley, et al.: The Structure of the Isomeric Quinoline Dicyanides; Journal of the American Chemical Society, vol. 73, No. 2, Feb. 15, 1951, pp. 772–774, XP002076934.

*Primary Examiner*—Gary Geist
*Assistant Examiner*—Jean F Volland

*Attorney, Agent, or Firm*—Kevin T. Mansfield

[57] ABSTRACT

The present invention provides a process for the production of an N,N-dialkylaminophenyl alkanol having the formula:

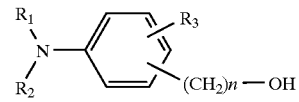

(1)

in which $R_1$ and $R_2$, independently, are $C_1$–$C_4$ alkyl, $R_3$ is hydrogen, halogen, cyano, $C_1$–$C_4$ alkyl or $C_1$–$C_4$ alkoxy and n is an integer from 1 to 4, comprising reacting an aminophenyl alkanol having the formula:

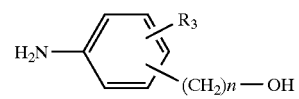

(2)

in which $R_3$ and n have their previous significance, with at least two moles of a dialkylsulfate having the formula:

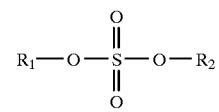

(3)

in which $R_1$ and $R_2$ have their previous significance. N,N-dialkylaminophenyl alkanols so obtained are valuable as intermediates for a wide range of end-products and are also useful, e.g., as accelerators for the peroxide-catalyzed polymerization of vinyl monomers, especially in polymerizable or curable formulations employed in dental applications.

25 Claims, No Drawings

PROCESS FOR THE PREPARATION OF N,N-DIALKYLAMINOPHENYL ALKANOLS

The present invention relates to a process for the production of N,N-dialkylaminophenyl alkanols.

N,N-dialkylaminophenyl alkanols are valuable intermediates for a wide range of end-products. For example, they find use as intermediates for 1,4-dihydropyridine derivatives having antihypertensive activity. N,N-dialkylaminophenyl alkanols are also valuable per se as accelerators for the peroxide-catalyzed polymerization of vinyl monomers, especially in polymerzable or curable formulations employed in dental applications, as described, for instance, in U.S. Pat. No. 4,284,551.

Methods have been already suggested for the production of N,N-dialkylaminophenyl alkanols. In U.S. Pat. No. 4,284,551, for example, 4-dimethylaminophenyl ethanol is synthesized by the reaction of 4-aminophenyl ethanol with methyl iodide. Moreover, in JACS, 97:11, May 28, 1975, at page 3106, 4-dimethylaminophenyl ethanol is synthesized by the reaction of 4-nitrophenyl ethanol with formaldehyde in ethanol in the presence hydrogen and a Pd/C catalyst at elevated pressure.

These known methods are disadvantageous for use in the industrial manufacture of N,N-dialkylaminophenyl alkanols in several respects, namely because of their use of expensive alkyl iodide, as alkylating agent, or by virtue of their use of elevated pressure and expensive catalyst, combined with the technical difficulties associated with the continuous monitoring of pH control in a high pressure environment.

Surprisingly, it has now been found that by the reaction of an aminophenyl alkanol with a dialkylsulfate, as alkylating agent, good yields of N,N-dialkylaminophenyl alkanols are obtained, while avoiding the disadvantages associated with known methods for the production of N,N-dialkylaminophenyl alkanols.

During the reaction an ammonium salt by-product is formed. If that by-product is subsequently decomposed by reacting with an amino compound the yields of N,N-dialkylaminophenyl alkanols can be further increased.

Accordingly, the present invention provides a process for the production of an N,N-dialkylaminophenyl alkanol having the formula:

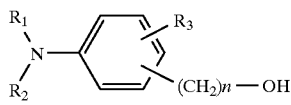

(1)

in which $R_1$ and $R_2$, independently, are $C_1$–$C_4$alkyl, $R_3$ is hydrogen, halogen, cyano, $C_1$–$C_4$alkyl or $C_1$–$C_4$alkoxy and n is an integer from 1 to 4, comprising reacting an aminophenyl alkanol having the formula:

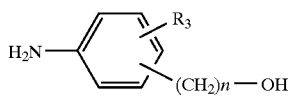

(2)

in which $R_3$ and n have their previous significance, with at least two moles of a dialkylsulfate having the formula:

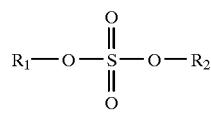

(3)

in which $R_1$ and $R_2$ have their previous significance.

In the reactants of formula (2), halogen substituents $R_3$ may be chlorine, bromine or iodine substituents; $C_1$–$C_4$alkyl substituents $R_3$ may be methyl, ethyl, n-propyl, isopropyl or n-butyl substituents; and $C_1$–$C_4$alkoxy substituents $R_3$ may be methoxy, ethoxy, isopropoxy or n-butoxy substituents. Preferably, however, $R_3$ is hydrogen and n is 2. Preferably, the substituent $(CH_2)_n$—OH is in the 4-position with respect to the amino group in the reactants of formula (2).

In the reactants of formula (3), $R_1$ and $R_2$, independently, may be methyl, ethyl, n-propyl, isopropyl or n-butyl substituents. Preferably, however, $R_1$ and $R_2$ are identical and each is methyl.

The process according to the present invention is preferably conducted in an aqueous medium and preferably at normal pressure, thus obviating the need for special high pressure reaction equipment. It is normally advantageous to use the dialkylsulfate having the formula (3) in a slight excess over the two moles stoichiometrically required for reaction with one mole of the aminophenyl alkanol having the formula (2), e.g. In an amount of from 2.05 to 2.4 moles per mole of the aminophenyl alkanol having the formula (2).

Since the possibility exists that the dialkylsulfate having the formula (3), instead of reacting at the desired amino group of the aminophenyl alkanol having the formula (2), could react at the undesired hydroxy group of the aminophenyl alkanol having the formula (2), it has been found to be advantageous to add the dialkylsulfate having the formula (3) in a portion-wise manner to the aminophenyl alkanol having the formula (2). In this way, the reaction of the dialkylsulfate having the formula (3) at the desired amino group of the aminophenyl alkanol having the formula (2) is optimised. Moreover, again with the objective of optimising the reaction of the dialkylsulfate having the formula (3) at the desired amino group of the aminophenyl alkanol having the formula (2), it has been found to be advantageous, after each portion-wise addition of the dialkylsulfate having the formula (3), to raise the pH value of the reaction mixture, preferably to a pH value within the range of from 3 to 5. The pH adjustment may be conveniently effected by the addition of an alkaline material such as an alkali metal hydroxide, an alkaline earth metal hydroxide, an alkali metal carbonate or an alkaline earth metal carbonate.

The process according to the present invention is preferably conducted at a temperature within the range of from 40 to 100° C., more preferably at a temperature within the range of from 50 to 95°0 C.

After completion of the reaction, the N,N-dialkylaminophenyl alkanol having the formula (1) may be separated from the reaction mixture by any convenient conventional technique. For instance, the separation of the N,N-dialkylaminophenyl alkanol having the formula (1) from the remaining components of the reaction mixture, such as water and inorganic salts, may be facilitated by the addition of a water-immiscible organic solvent such as. n-hexane, toluene, xylene or ethyl acetate and a phase transfer catalyst such as tetrabutylammonium bromide. The organic layer, containing the N,N-dialkylaminophenyl alkanol having the formula (1), may then be dried prior to the isolation of the N,N-dialkylaminophenyl alkanol having the formula (1), e.g. by distillation. The crude N,N-dialkylaminophenyl alkanol having the formula (1) so obtained may then be purified by any conventional technique such as column separation or recrystallization.

In a preferred embodiment, the aqueous layer, containing the concomitantly-produced quaternary ammonium salt of an N,N-dialkylaminophenyl alkanol having the formula (1), is reacted with an amino compound to produce further N,N-dialkylaminophenyl alkanol having the formula (1). For example, in a preferred process according to the present invention, the quaternary ammonium salt by-product has the formula:

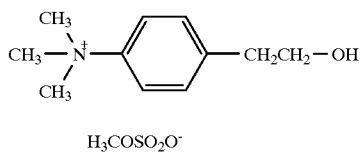

The amino compound used for the reaction with the quaternary ammonium salt is preferably a primary amine $R_4$-$NH_2$ or a secondary amine $(R_4)_2NH$ in which $R_4$ is an aliphatic or an aromatic group. Preferred aliphatic groups $R_4$ are optionally substituted $C_1$–$C_4$ alkyl groups, especially hydroxy-substituted $C_1$–$C_4$ alkyl groups or amino-substituted $C_1$–$C_4$ alkyl groups. Examples of such aliphatic primary amines $R_4$-$NH_2$ include methylamine, ethylamine, n-propylamine, sec-propylamine, t-butylamine and ethylenediamine and, in particular, ethanolamine. Aniline and substituted aniline compounds such as methyl- or hydroxy-anilines, are examples of aromatic primary amines $R_4$-$NH_2$. The secondary amine $(R_4)_2NH$ is preferably an aliphatic secondary amine and may be, e.g., dimethylamine, diethylamine, di-n-propylamine, di-sec-propylamine, di-t-butylamine or diethanolamine.

The reaction between the preferred quaternary ammonium salt and a preferred amino compound, ethanolamine, may be represented by the following scheme:

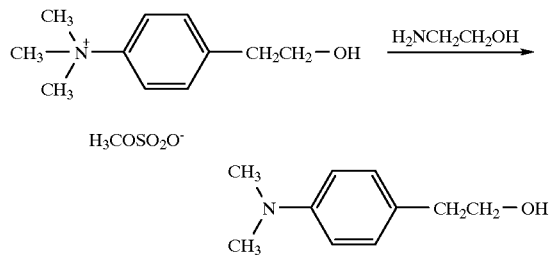

The reaction between the quaternary ammonium salt and the amino compound is preferably conducted at an elevated temperature, most conveniently at the boiling temperature of the reaction mixture, and under acidic conditions, preferably at a pH value below 6, especially at a pH value in the range of from 3.5 to 5.5.

The following Examples further illustrate the present invention. Parts and percentages shown therein are by weight unless otherwise stated.

EXAMPLE 1

137.2 g of 2-(4-aminophenyl)-ethanol are mixed with 200 g of water and the mixture is heated to 60° C. At this temperature, there are added, at a rate of 3.8 g/minute, 152 g of dimethylsulfate, whereupon the temperature of the reaction mixture rises to 85° C. A black solution is obtained. The reaction temperature Is held at 85° C. for 1 hour, during which time the pH value of the reaction mixture falls to 1.0.

The pH value of the reaction mixture is adjusted to 4.0 by the addition of 70 g of 22% aqueous sodium hydroxide solution. After allowing the reaction mixture to stand for 20 minutes, a further 88 g of dimethylsulfate are added, whereupon the temperature of the reaction mixture rises to 89° C. The reaction mixture is held at this temperature for 1 hour and then the pH value of the reaction mixture is adjusted to 4.0 using aqueous sodium hydroxide solution. After stirring the reaction mixture for 20 minutes the third and final portion (31.5 g)of dimethylsulfate is added and the whole mixture is stirred for a further 16 hours at 90° C. The temperature of the reaction mixture is reduced to 60° C. and the pH is adjusted to 5.0 using aqueous sodium hydroxide solution. 300 ml of ethyl acetate are added and, after stirring the mixture for 10 minutes, the reaction mixture is allowed to separate into two phases. The upper phase consists of N,N-dimethylaminophenylethanol, ethyl acetate and impurities and the lower phase consists of water and salt The upper phase is evaporated in a rotary evaporator to give a brown oil which is purified by means of column chromatography.

The column conditions used are as follows:

column filling: silica gel (0.025–0.04)

filling height: 20 cm eluent: hexane/ethyl acetate (3:1)

working pressure: 0.2 bar.

Four fractions are obtained, the third of which contains the desired product, N,N-dimethylaminophenylethanol having m.pt. 56–57° C., in a yield 50%, and having the following NMR data:

$^1$H-NMR [ppm]: 1.36; 3.79; 2.76; 7.09; 6.70; 2.91 in $CDCl_3$; $^{13}$C-NMR [ppm]: 63.9; 38.1; 126.2; 129.6; 113.1; 149.4; 40.8.

Example 2

Under a nitrogen atmosphere and with the exclusion of light, 400 ml of toluene, 150 ml of water and 1.4 g of tetrabutylammonium bromide are added to 68.6 g of of 2-(4-amino-phenyl)-ethanol. The mixture is stirred at 300 rpm and heated to 30° C. At this temperature, there are added, to the reaction mixture, 130 ml of dimethyl sulfate, at a rate of 1 ml/min., while maintaining the pH value of the reaction mixture at 6.0 by the addition of 80 ml of 50% aqueous sodium hydroxide solution. During the addition, the internal temperature of the reaction mixture rises to 36–37° C. The reaction mixture is then stirred for 15 minutes until the pH value of the mixture ceases to fall. The reaction is completed when no monomethylaminophenylethanol can be detected chromatographically, under UV 254, in the upper phase of the reaction mixture. The pH value of the reaction mixture is adjusted to 6.5 with a little NaOH and the mixture is stirred for 1 hour to decompose excess dimethyl sulfate. The stirrer is then switched off, whereupon two well-separated phases of the reaction mixture are obtained. The upper phase (420 ml) is light brown and consists of toluene and product; the lower phase (400 ml) is brown and consists of water and product.

The aqueous phase is extracted twice with 150 ml of toluene, all the toluene phases are combined and the toluene solvent is removed to leave 30 g of a brown oil which solidifies at 40° C. This residue is treated with 800 ml of n-hexane and 6 g of silica gel, the resulting mixture is heated to 68 ° C., held at this temperature for 30 minutes and filtered through a preheated funnel. The resulting clear filtrate Is cooled with stirring. At 50° C., the product begins to crystallise out as white needles. The mixture is cooled to 15° C., stirred for 1 hour and filtered. In this way, there are obtained 21 g (25% theory) of dry N,N-dimethylamino-phenylethanol, the purity of which is determined by gas chromatography.

The aqueous phase (400 ml) is heated to 80° C., treated with 300 ml of ethanolamine and the mixture is boiled for at least 2 hours at 106–108° C. The mixture is cooled to 80° C. and the pH value of the mixture is adjusted to 4.5 with 185 ml of 60% sulfuric acid, whereupon the temperature of the mixture rises to 95° C. The mixture is cooled to 60° C. and the resulting product is extracted with 300 ml of toluene. The resulting aqueous phase is again extracted with 150 ml of toluene. The toluene phases are combined and the toluene is removed by distillation to leave 60 g of N,N-dimethylaminophenylethanol (45 g of pure material after recrystallisation), representing a yield of about 80% of theory.

EXAMPLE 3

The process described in Example 2 is repeated, working in exactly the same way, but using an equimolar amount of ethylenediamine instead of ethanolamine to decompose the by-product.

N,N-dimethylaminophenylethanol is obtained in similar purity and yield.

We claim:

1. A process for the production of an N,N-dialkylaminophenyl alkanol having the formula:

$$\underset{R_2}{\overset{R_1}{\diagdown}} N - \underset{}{\underset{}{\diagup}} \underset{}{\diagdown} \underset{(CH_2)_n-OH}{\overset{R_3}{\diagup}} \quad (1)$$

in which $R_1$ and $R_2$, independently, are $C_1$–$C_4$alkyl, $R_3$ is hydrogen, halogen, cyano, $C_1$–$C_4$alkyl or $C_1$–$C_4$alkoxy and n is an integer from 1 to 4, comprising reacting an aminophenyl alkanol having the formula:

$$H_2N-\underset{}{\underset{}{\diagup}} \underset{}{\diagdown} \underset{(CH_2)_n-OH}{\overset{R_3}{\diagup}} \quad (2)$$

in which $R_3$ and n have their previous significance, with at least two moles of a dialkylsulfate having the formula:

$$R_1-O-\underset{\underset{O}{\|}}{\overset{\overset{O}{\|}}{S}}-O-R_2 \quad (3)$$

in which $R_1$ and $R_2$ have their previous significance, wherein the process is conducted in an aqueous medium at normal pressure.

2. A process according to claim 1 in which, in the reactant of formula (2), $R_3$ is hydrogen and n is 2.

3. A process according to claim 1 in which the substituent $(CH_2)_n$—OH is in the 4-position with respect to the amino group in the reactants of formula (2).

4. A process according to claim 1 in which, in the reactant of formula (3), $R_1$ and $R_2$ are identical and each is methyl.

5. A process according to claim 1 in which the dialkyl-sulfate having the formula (3) is used in an amount of from 2.05 to 2.4 moles per mole of the aminophenyl alkanol having the formula (2).

6. A process according to claim 1 in which the dialkyl-sulfate having the formula (3) is added in a portion-wise manner to the aminophenyl alkanol having the formula (2).

7. A process according to claim 1 in which, after each portion-wise addition of the dialkylsulfate having the formula (3), the pH value of the reaction mixture is raised to a pH value within the range of from 3 to 5.

8. A process according to claim 7 in which the pH adjustment is effected by the addition of an alkaline material.

9. A process according to claim 8 in which the alkaline material is an alkali metal hydroxide, an alkaline earth metal hydroxide, an alkali metal carbonate or an alkaline earth metal carbonate.

10. A process according to claim 1 in which the process is conducted at a temperature within the range of from 40 to 100° C.

11. A process according to claim 10 in which the process is conducted at a temperature within the range of from 50 to 95° C.

12. A process according to claim 1 in which, after completion of the reaction, the N,N-dialkylaminophenyl alkanol having the formula (1) is separated from the reaction mixture by the addition of a water-immiscible organic solvent and a phase transfer catalyst, to produce an organic layer and an aqueous layer.

13. A process according to claim 12 in which the organic solvent is n-hexane, toluene, xylene or ethyl acetate and the phase transfer catalyst is tetrabutylammonium bromide.

14. A process according to claim 12 in which the aqueous layer, containing the concomitantly-produced quaternary ammonium salt of an N,N-dialkylaminophenyl alkanol having the formula (1), is reacted with an amino compound to produce further N,N-dialkylaminophenyl alkanol having the formula (1).

15. A process according to claim 14 in which the quaternary ammonium salt by-product has the formula:

$$\underset{CH_3}{\overset{CH_3}{\diagdown}} \overset{+}{N} - \underset{}{\underset{}{\diagup}} \underset{}{\diagdown} - CH_2CH_2-OH$$
$$H_3COSO_2O^-$$

16. A process according to claim 14 in which the amino compound used for the reaction with the quaternary ammonium salt by-product is a primary amine $R_4$—$NH_2$ or a secondary amine $(R_4)_2NH$ in which $R_4$ is an aliphatic or an aromatic group.

17. A process according to claim 16 in which the aliphatic group $R_4$ is an optionally substituted $C_1$–$C_4$ alkyl group.

18. A process according to claim 17 in which the substituted $C_1$–$C_4$ alkyl group is a hydroxy-substituted $C_1$–$C_4$ alkyl group or an amino-substituted $C_1$–$C_4$ alkyl group.

19. A process according to claim 16 in which the aliphatic primary amine $R_4$—$NH_2$ is methylamine, ethylamine, n-propylamine, sec-propylamine, t-butylamine, ethylenediamine or ethanolamine.

20. A process according to claim 16 in which the aromatic primary amine $R_4$—$NH_2$ is aniline or a substituted aniline compound.

21. A process according to claim 16 in which the secondary amine $(R_4)_2NH$ is an aliphatic secondary amine.

22. A process according to claim 21 in which the aliphatic secondary amine is dimethylamine, diethylamine, di-n-propylamine, di-sec-propylamine, di-t-butylamine or diethanolamine.

23. A process according to claim 14 in which the reaction between the quaternary ammonium salt and the amino compound is conducted at an elevated temperature and under acidic conditions.

24. A process according to claim 23 in which the process is conducted at the boil and at a pH value below 6.

25. A process according to claim 24 in which the process is conducted at a pH value in the range of from 3.5 to 5.5.

* * * * *